United States Patent [19]

Finney

[11] 4,417,545

[45] Nov. 29, 1983

[54] PACKAGE FOR THE TRANSPORTATION OF NEMATODES

[75] Inventor: Jean R. Finney, St. John's, Canada

[73] Assignee: Memorial University of Newfoundland, Newfoundland, Canada

[21] Appl. No.: 347,769

[22] Filed: Feb. 11, 1982

[30] Foreign Application Priority Data

Sep. 21, 1981 [CA] Canada ................................. 386306

[51] Int. Cl.³ ............................................. A01K 67/00
[52] U.S. Cl. ........................................... 119/1; 119/15
[58] Field of Search ............................. 119/1, 2, 3, 15

[56] References Cited

U.S. PATENT DOCUMENTS

| | | | |
|---|---|---|---|
| 3,194,211 | 7/1965 | Stanek | 119/3 |
| 3,499,420 | 3/1970 | Atwell | 119/1 |
| 4,192,254 | 3/1980 | Apel | 119/1 |
| 4,334,498 | 6/1982 | Bedding | 119/1 |

*Primary Examiner*—Hugh R. Chamblee

*Attorney, Agent, or Firm*—Millen & White

[57] ABSTRACT

A novel method and package for both storing and shipping of nematodes and/or nematode eggs in their dormant state for the biological control of insects is provided herein. The package comprises: (1) a water-impervious container having a removable cover; (2) at least one pair of discrete, formed, substrates, each comprising an open celled, light weight foam having wicking action, the substrates substantially filling, and disposed in the container and below the cover, the foam being capable of retaining water within the foam, and when soaked in distilled water, of providing a distilled water having a pH of about 5 to about 7, the pair of substrates being disposed in face-to-face relationship; and at least one storage cavity at the interface between the pair of substrates for the placement therein of nematodes and/or nematode eggs in their dormant state, the wicking action of the foam serving to maintain the nematodes and/or nematode eggs moist. This enables the safe storage and transport of the nematodes for biological and agricultural use.

10 Claims, 2 Drawing Figures

PACKAGE FOR THE TRANSPORTATION OF NEMATODES

BACKGROUND OF THE INVENTION (i) Field of the Invention

This invention relates to the use of namatodes for the biological control of insects. More particularly, it relates to an efficient, inexpensive method and means of shipping the namatodes to the site where they are to effect such biological control.

*Romanomermis culicivorax* is a mermithid nematode which can be mass produced in vivo and is now in use as a biological control agent against warm climate mosquitoes.

(ii) Description of the Prior Art

In the past, the transportation of the nematode eggs was in a composition formulated in sand. This made the control agent expensive because the ratio of sand to nematode eggs was high and hence the relative weight of sand increased transportation costs enormously. It was also found that the sand formulations were inefficient. There could be some loss of nematodes and their eggs due to grinding mechanical damage by shifting of the sand. If condensation occurred within the plastic wrapping around the nematode eggs, the extra water could cause the eggs to hatch prematurely. As the preparasites are short lived, they undoubtedly would die before they could be used. In addition, there was a danger of fungal infection thriving in such a situation. Alternatively, the sand could dry out completely, thus completely causing death of the eggs.

It is also known that *Neoaplectana carpocapsae* has activity againt many insect population, including Colorado potato beetle *Leptinotarsa decemlineata, Dysdercus peruvianus* (Hemiptera), Tobacco budworm *Heliothis virescens,* Codling moth *Laspayresia pomonella,* Cabbage root maggot *Hylemyl brassicae,* European corn borer *Ostrinia nubilalis,* Corn earwarm *Helicoverpa zea,* Imported cabbage worm *Pieric rapae,* Pale apple leaf roller *Pseudexendera mali,* Winter moth *Operophtera brumata,* Cutworm *Pseudaletia separata,* Paddy cutworm *Cirphis compta,* Nantucket pine tip moth *Rhyacionia frustrana,* Sourhern pine beetle *Dendroctonus frontalis,* Wireworm *Agriotes* sp., Pear aphids, Leaf beetles, Ladybird larvae, Root fly larvae, Rice stem borer *Chilo* sp., Whitefringed beetle *Graphognathus peregrinus,* Formosan termite *Coptotermes formosanus,* onion borer *Acrolepia assectella,* Hylemya spp., Pecan weevil *Curculio caryae, Spodoptera frugiperda,* Rice stem borer, Navel orangeworm *Paramyelois transitella,* Wireworms *Agritoes lineatus,* and *Selatoscmus aeneus.*

The art has been faced with the problem of safety and efficiently storing and transporting the nematodes. For mermithid, e.g., Mosquito parasitic mermithids including *Romanomermis culicivorax, R. nielseni, Octomyomermis muspratti,* and for Blackfly parasitic mermithids including several species of Mesomermis, Hydromermis and Isomermis, the eggs need to be transported for use in the biological control of mosquitoes and blackflies. For other, particularly rhabditid, nematodes, e.g., the Breton and DD-136 strains of *Neoaplectana carpocapsae* and *Heterorhabditis heliothidis,* the infective stage of the worm would be transported for use as parasites of a wide range of agricultural and forest pests including *Choristoneura fumiferana,* the spruce budworm and *Scolytus scolytus,* the vector of Dutch Elm Disease.

These nematodes can be mass produced on a commercial scale but storing and shipping is a problem. Thus, it is known that an efficient, inexpensive method of shipping *N. carpocapsae* and other rhabditids is difficult to achieve. The most important aspect involved in shipping such nematodes was believed to be able to provide enough air to keep them alive en route. This was said to be achieved by plugging the containers with cotton and avoiding the use of water as a shipping medium. It was also suggested that good methods might be to place the infective stages on some inert substances (charcoal, wood chips) that could be kept moist or indeed to transport the infective nematodes within the host cadaver. However, it was known that the nematodes should be able to be removed easily from the substrate in water when ready for application.

SUMMARY OF THE INVENTION (i) Aims of the Invention

Accordingly, there is a need for, and it is an object of this invention to provide, an improved system and method for the transportation of nematodes and/or nematode eggs, particularly one which does not require the use of sand.

(ii) Statements of Invention

By this invention, a packing for storing and/or shipping nematodes and/or nematode eggs in the dormant state is provided comprising: (1) a water-imprevious container having a removable cover; (2) at least one pair of discrete, formed, substrates, each comprising an open celled, light weight foam having wicking action, the substrates substantially filling, and disposed in the container and below the cover, the foam being capable of retaining water within the foam, and when soaked in distilled water, of providing a distilled water having a pH of about 5 to about 7, the pair of substrates being disposed in face-to-face relationship; and at least one storage cavity at the interface between the pair of substrates for the placement therein of nematodes and/or nematode eggs in their dormant state, the wicking action of the foam serving to maintain the nematodes and/or nematode eggs moist.

By this invention also, a package for storing and/or shipping nematodes and/or nematodes eggs at least one pair of discrete, formed, substrates, each comprising an open celled, light weight foa having wicking action, the substrates substantially filling, and disposed in the container and below the cover, the foam being capable of retaining water within the foam, and when soaked in distilled water, of providing a distilled water having a pH of about 5 to about 7, the pair of substrates being disposed in face-to-face relationship; and at least one storage cavity at the interface between the pair of substrates for the placement therein of nematodes and/or nematode eggs in their dormant state, the wicking action of the foam serving to maintain the nematodes and/or nematode eggs moist; a quantity of distilled water absorbed by the foam; and a sealing wrapper for the covered, closed container which contains the nematodes and/or nematode eggs in the dormant state. is provided comprising: (1) a water-impervious container having a removable cover; (2) a substrate comprising an open celled, light-weight foam having wicking action substantially filling and disposed in each of the container and the cover, the two substrates being disposed in face-to-face relationship; (3) at least one storage cavity at the interface between the two substrates, the namatodes and/or nematode eggs and/or infective stage nematodes still enclosed within a host cadaver being placed therein and being sandwiched between the two substrates; (4) a mass of distilled water absorbed by the foam; and (5) a wrapper for the covered, closed container containing the nematodes and/or namatode eggs and/or infective stage nematodes still enclosed within a host cadaver.

By this invention also, a method is provided for shipping and/or storing nematodes and/or nematode eggs in their dormant state comprising: (A) placing nematodes and/or nematode eggs in their dormant state within at least one storage cavity in a package comprising a water impervious container having a removable cover, at least one pair of discrete, formed, substrates, each comprising an open celled, light weight foam having wicking action, the substrates substantially filling, and disposed in the container and below the cover, the form being capable of retaining water within the foam, and when soaked in distilled water, of providing a distilled water having a pH of about 5 to about 7, the pair of substrates being disposed in face-to-face relationship, and at least one storage cavity at the interface between the pair of substrates for the placement therein of nematodes and/or nematode eggs in their dormant state, the wicking action of the foam serving to maintain the nemotodes and/or nematode eggs moist; placing a quantity of distilled water within the at least one cavity to be absorbed by the foam; closing the container; and wrapping and sealing the closed container which now contains the nematodes and/or nematode eggs in their dormant state.

(iii) Features of the Invention

By one feature thereof, the substrate is an inert fluorofoam having a small pore size.

By another feature, the nematodes are in the egg form.

By a further feature, several thabditid nematodes are provided therein.

By a still further feature, a plurality of storage cavities are provided.

By a further feature, the nematodes are the eggs of *Romanomermis culicivorax,* and the substrate is an inert fluorofoam having a small pore size.

By yet another feature thereof, the nematodes are of the worm of *Neoaplectana carpocapsae* or strains thereof and the substrate is an inert fluorofoam having a small pore size.

Thus, by the invention, the nematodes and/or nematode eggs and/or infective stage nematodes still enclosed in a host cadaver can be transported more economically in a substance other than sand. The nematodes can be mass collected, concentrated and stored in water. Massive numbers of such eggs can be transported and kept in a damp, but not wet, environment in a smaller and lighter weight container than previously used.

BRIEF DESCRIPTION OF THE DRAWINGS

In the accompanying drawings.

DESCRIPTION OF PREFERRED EMBODIMENTS OF THE INVENTION

Figure 1:
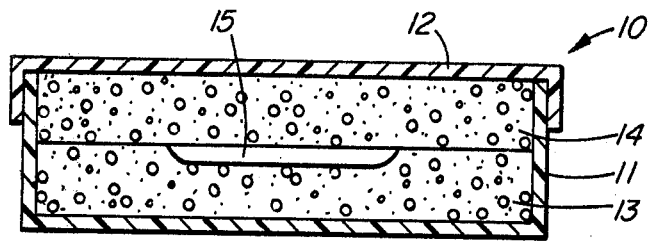
FIG. 1 is a cross-sectional view of a shipping package of one embodiment of the invention in its empty configuration.

As seen in FIG. 1, the package comprises a water-impervious container 11, formed, e.g., of a synthetic plastics material, for example, polystyrene or a polyacrylate, and a removable cover 12 usually formed of the same material. An open-celled, light-weight foam material having wicking action, e.g., an inert fluorofoam having a small pore size, substantially fills the container, i.e., substrate 13, and the cover, i.e., substrate 14. The two substrates 13 and 14 are in face-to-face relationship. At least one storage cavity 15 is at the interface between the two substrates 13 and 14.

Figure 2:
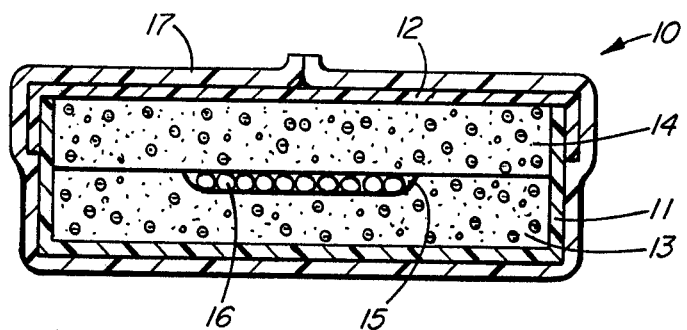
FIG. 2 is a cross-sectional view of a shipping package of another embodiment of this invention in its loaded configuration.

As seen in FIG. 2, the cavity 15 is filled with nematodes and/or nematode eggs 16. A mass of water is absorbed by the foam, and a sealing wrapper 17 envelopes the covered, closed container.

DESCRIPTION OF PREFERRED EMBODIMENTS

The following are Examples of this invention.

Firstly, nine samples of foam were tested for their suitability as follows:
1. A block of foam was left to soak overnight in distilled water.
2. The pH of the water around the foam was taken and any discoloration of the water was noted.
3. The soaked foam was sliced to fit 100×20 mm petri dishes, and surplus water was sucked off.
4. Five hundred fully embryonated nematode eggs were placed in a depression made in the lower portion of the foam, the upper half was fitted over and the petri dish was sealed with parafilm.
5. Two replicates were left at room temperature (approx. 24° C.) and two replicates were incubated at 10° C.
6. At the end of the second week, an attempt was made to hatch the eggs from one replicate at room temperature by flooding with distilled water. Just before flooding, the eggs were observed for any signs of discoloration, fungal infection, etc. The hatching procedure was repeated at the end of one month with the second room temperature replicate. Those eggs being held at 10° C. were provided for investigation of long-term storage effects.

The results of these tests are given below in the following Table.

| Name of Product | Colour | pH | Comments |
| --- | --- | --- | --- |
| FilFast Foam | green | 6.6 | |
| FilFast Foam | white | 4.3 | |
| FilFast Rose Foam Plus | white | 6.2 | Urea-formaldehyde resin. Contains Rogard-flower life extender. Pink colour around eggs. |
| FilFast Bar-Fast | black | 10.2 | Contains adhesives |
| FilFast Lava Foam | black | 4.9 | |
| FilFast Ole Foam | green | 8.9 | |
| Oasis Deluxe | dark green | 3.8 | Water discoloured. |
| Oasis | dark green | 3.8 | Phenolic foam - water discoloured. |
| SelFast | green | 5.1 | |

All these foams are Registered Trade Marks

It was found that none of the foams tested, except SelFast, proved suitable for the safe packaging of nematodes when in the nematode egg form. Of these tested, some contained additives; some contained dyes which negatively affected the eggs; and the composition of some of the foams proved poisonous to the eggs. Combinations of the above resulted in a very acid or very alkaline water pH in which the egg died. Only eggs held on SelFast produced a significant hatch on demand. However, all the foams are believed to be suitable for the packaging of nematodes when in the infectious stage still enclosed in the host cadaver.

The following tests on the viability of the transportation of nematode eggs were carried out.

Packages of the nematode eggs prepared as described above according to an embodiment of this invention were shipped from St. John's, Newfoundland. The containers were petri dishes, with the substrate being cut to fit within the dish. A flat piece of plastic was sealed with masking tape over the top of the container. The container was placed in a cardboard box with Styrofoam chips and packaged for shipping.

It was found that there was no damage to the package or sign of leakage. Twenty-four hours after opening, very low counts were found. However, one day later, counts were increasing and were comparable to controls. Within three days, all the counts were comparable to controls, i.e., 80-90%.

Thus, it has been shown that nematode eggs prestored at 5° C. at stage (6) can be transported. The amount of the water around the eggs is important.

SUMMARY

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

I claim:

1. A shipping and/or storage package for shipping and/or storing nematodes and/or nematode eggs in their dormant state, consisting essentially of
   (1) a water-impervious container having a removable cover;
   (2) at least one pair of discrete, formed, substrates, each comprising an open celled, light weight foam having wicking action, said substrates substantially filling, and disposing in said container and below the cover, said foam being capable of retaining water within said foam, and when soaked in distilled water, of providing distilled water having a pH of about 5 to about 7, said pair of substrates being disposed in face-to-face relationship;
   and
   (3) at least one storage cavity at the interface between said pair of substrates for the placement therein of nematodes and/or nematode eggs in their dormant state, said wicking action of said foam serving to maintain said nematodes and/or nematode eggs moist.

2. The shipping and/or storage package of claim 1 wherein said substrate is an inert fluorofoam having a small pore size.

3. A shipping and/or storage package for shipping and/or storing nematodes and/or nematode eggs in their dormant state, consisting essentially of
   (1) a water-impervious container having a removable cover; (2) at least one pair of discrete, formed, substrates, each comprising an open celled, light weight foam having wicking action, said substrates substantially filling, and disposed in said container and below the cover, said foam being capable of retaining water within said foam, and when soaked in distilled water, of providing distilled water having a pH of about 5 to about 7, said pair of substrates being disposed in face-to-face relationship;
   (3) at least one storage cavity at the interface between said pair of substrates for the placement therein of nematodes and/or nematode eggs in their dormant state, said wicking action of said foam serving to maintain said nematodes and/or nematode eggs moist;
   (4) a quantity of distilled water absorbed by said foam:
   and
   (5) a sealing wrapper for said covered, closed container which container contains said nematodes and/or nematode eggs in the dormant state.

4. The package of claim 3 wherein the nematodes are in the egg form.

5. The package of claim 3 wherein several thabditid nematodes are provided therein.

6. The package of claim 3 wherein a plurality of storage cavities are provided.

7. The package of claim 3 wherein said nematodes are the eggs of *Romanomermis culcivorax*, and wherein said substrate is an inert fluoroform having a small pore size.

8. The package of claim 3 wherein said nematodes are of the worm of *Neoplectana carpocapsae* or strains thereof, and wherein said substrate is an inert fluorofoam having a small pore size.

9. A method for shipping and/or storing nematodes and/or nematode eggs in their dormant state comprising the steps of:
   (A) placing nematodes and/or nematode eggs in their dormant state within at least one storage cavity in a package comprising
      (1) a water-impervious container having a removable cover,
      (2) at least one pair of discrete, formed, substrates, each comprising an open celled, light weight foam having wicking action, said substrates substantially filling, and disposed in said container and below the cover, said foam being capable of retaining water within said foam, and when soaked in distilled water, of providing distilled water having a pH of about 5 to about 7, said pair of substrates being disposed in face-to-face relationship,
   and
      (3) at least one storage cavity at the interface between said pair of substrates for the placement therein of nematodes and/or nematode eggs in their dormant state, said wicking action of said foam serving to maintain said nematodes and/or nematode eggs moist;
   (B) placing a quantity of distilled water within said at least one cavity to be absorbed by said foam;
   (C) closing the container;
   and
   (D) wrapping and sealing said closed container which now contains said nematodes and/or nematode eggs in their dormant state.

10. A method according to claim 9, wherein said open-celled, light weight foam is an inert fluorofoam.

* * * * *